United States Patent
Yan (10) Patent No.: US 7,490,988 B1
(45) Date of Patent: Feb. 17, 2009

(54) SYSTEMS AND METHODS FOR PATIENT SPECIFIC PIXEL SPACING CALIBRATION FOR MAMMOGRAPHY X-RAY

(75) Inventor: John Yan, Libertyville, IL (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/051,657

(22) Filed: Mar. 19, 2008

(51) Int. Cl.
*G01D 18/00* (2006.01)

(52) U.S. Cl. .......... 378/207; 378/37; 378/901; 382/131

(58) Field of Classification Search ........ 378/4–27, 378/37, 62, 207, 901; 382/130–132
See application file for complete search history.

(56) References Cited

U.S. PATENT DOCUMENTS

| | | | |
|---|---|---|---|
| 3,971,950 A | 7/1976 | Evans et al. | 378/37 |
| 5,335,257 A | 8/1994 | Stunberg | 378/37 |
| 6,718,056 B1 | 4/2004 | Bothorel et al. | 382/128 |
| 7,203,348 B1 | 4/2007 | Karssemeijer et al. | 382/128 |
| 2006/0098855 A1* | 5/2006 | Gkanatsios et al. | 382/128 |
| 2006/0167355 A1 | 7/2006 | Rico et al. | |

\* cited by examiner

*Primary Examiner*—Courtney Thomas
(74) *Attorney, Agent, or Firm*—McAndrews, Held & Malloy, Ltd.; Peter J. Vogel; Michael A. Dellapenna (57) ABSTRACT

Certain embodiments of the present invention provide methods and systems for calibrating a pixel spacing attribute value for X-ray mammography imaging based on a patient-specific breast thickness value. Certain embodiments provide a method for patient specific pixel spacing calibration for mammography X-ray imaging. The method includes determining a patient specific breast thickness value for a particular patient being imaged by a mammography X-ray device having a radiation source and a detector and an associated imager pixel spacing value. The method also includes calibrating a pixel spacing attribute for a mammography X-ray image based on the patient specific breast thickness value, a radiation source to detector distance in the mammography X-ray device, and the image pixel spacing value.

20 Claims, 3 Drawing Sheets

SYSTEMS AND METHODS FOR PATIENT SPECIFIC PIXEL SPACING CALIBRATION FOR MAMMOGRAPHY X-RAY

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to imaging system calibration. In particular, the present invention relates to calibration of pixel spacing based on the patient in an X-ray mammography system.

Medical diagnostic imaging systems encompass a variety of imaging modalities, such as X-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as X-rays passing through a patient, for example. The generated images may be used for many purposes.

In order to help ensure that medical diagnostic images are reliable, it is advantageous to calibrate medical diagnostic imaging systems. The calibration of imaging systems is important for several reasons, including image quality, measurement accuracy and system performance. Inaccuracies in an imaging system may result in blurring, streaking, or introduction of ghost images or artifacts in the resulting image. Poor image calibration may prevent reliable analysis of an image. The calibration of medical imaging systems may help to produce a distinct and usable representation of an object.

The Digital Imaging and Communication in Medicine (DICOM) standard provides rules and guidelines for medical image acquisition, transmission, storage, and retrieval. These rules, guidelines, and other limitations impact how imaging systems and other related systems, such as reviewing and/or processing workstations, acquire and process images. For example, DICOM specifies a Digital X-ray (DX) Detector Distance Source to Patient Type 3 Implementation limitation. In a magnification mode, the value is equal to a distance in millimeters from the source to a theoretical average breast height (e.g., 20 mm above the breast support). In a contact mode, the value is equal to a distance in millimeters from the source to the detector plane.

As another example, in DICOM, an Estimated Radiographic Magnification factor Type 3 and a Distance Source to Entrance are computed based on the Distance Source to Patient. A DX Detector Imager Pixel Spacing Type 1 Implementation limitation specifies that the value is equal to a physical distance measured at a theoretical average breast height (e.g., 20 mm above the breast support) between the centers of each projected image pixel.

The Integrating the Healthcare Enterprise (IHE) is an initiative by healthcare professionals to improve sharing of information between healthcare computer systems. IHE coordinates and promotes use of established standards, such as DICOM, to facilitate communication and effective use of information for healthcare purposes. IHE is developing profiles to define requirements for certain system and/or certain behavior. For example, IHE is developing an IHE Mammography Image Profile (IHE Mammo) to define mammography requirements for display on Picture Archiving and Communication Systems (PACS) and third-party workstations. The profile includes recommendations regarding viewing of mammography images including image size, pixel spacing, etc.

Many third-party workstation and PACS vendors have received FDA clearance for their viewing stations to be used for digital mammography, which has introduced a variety of interconnectivity and interoperability issues with digital mammography imaging systems. The IHE Mammo profile helps to address these interconnectivity and interoperability issues for image acquisition and display.

One issue for interoperability is displayed image size, particularly when current and prior images have been obtained on different equipment. Regardless of the physical size of the detector plate, pixels, or gantry geometry, images should be displayed with the same relative physical size to radiologists. The DICOM standard already requires that the necessary attributes be present and completed. The IHE Mammo profile requires that a workstation make use of those attributes. Thus, correctness of those attributes is an important issue that needs to be address, but has not yet been in several circumstances.

An Imager Pixel Spacing (0018,1164) attribute is defined to specify a physical distance measured at a front plane of an image receptor housing between a center of each pixel. Pixel Spacing (0028,0030) is an attribute specifying a physical distance in a patient between a center of each pixel. However, displays often vary in choosing Imager Pixel Spacing (0018, 1164) or Pixel Spacing (0028,0030) as the basis for performing measurements, display, and/or printing. Thus, correlation or use of these values needs to be addressed.

In certain mammography X-ray systems, a calibration plane lies at a front plane of the X-ray system detector housing. An image acquired without a zoom bench may include the following parameters:
Detector Active Dimension(s) 250, 286
Distance Source to Detector
Distance Source to Patient
Estimated Radiographic Magnification 1
Imager Pixel Spacing 7.000E-2
Pixel Spacing 7.000E-2.

A image acquired with a zoom bench may include the following parameters:
Distance Source to Detector
Distance Source to Patient
Estimated Radiographic Magnification 1.8
Imager Pixel Spacing 7.000E-2
Pixel Spacing 3.890E-2.

In certain mammography X-ray systems, a calibration plane lies somewhere above a front plane of the X-ray system detector housing. An image acquired without a zoom bench may include the following parameters:
Field of View Dimension(s) 286, 233
Distance Source to Detector 650
Distance Source to Patient 636
Estimated Radiographic Magnification 1.022
Imager Pixel Spacing 7.000E-2.

A image acquired with a zoom bench may include the following parameters:
Distance Source to Detector 650
Distance Source to Patient 392
Estimated Radiographic Magnification 1.6582
Imager Pixel Spacing 7.000E-2.

In certain mammography X-ray systems, a calibration plane lies 20 mm above a front plane of the X-ray system detector housing. An image acquired without a zoom bench may include the following parameters:

Field of View Dimension(s) 306, 239
Distance Source to Detector 660
Distance Source to Patient 660
Estimated Radiographic Magnification 1
Imager Pixel Spacing 0.09409091.

A image acquired with a zoom bench may include the following parameters:

Distance Source to Detector 660
Distance Source to Patient 366
Estimated Radiographic Magnification 1.8
Imager Pixel Spacing 5.545E-2.

The data above illustrates problems with IHE Mammo profile section 4.16.4.2.2.1.1.3, in which Imager Pixel Spacing (0018,1164) and Estimated Radiographic Magnification Factor (0018,1114) are used to estimate the physical size of the image pixels in the patient body. The physical size of the pixels in an image for the purposes of distance measurements and the display of a distance caliper shall be approximated using the values of Imager Pixel Spacing (0018,1164) divided by Estimated Radiographic Magnification Factor (0018,1114). However, implementing that part of IHE Mammo profile will cause a "double correction" to certain mammography images.

Additionally, DICOM CP-586 clarified that Pixel Spacing (0028,0030) is allowed in projection X-ray and DX family images, CP-586 specifies that Pixel Spacing (0028,0030) shall have the same values as Imager Pixel Spacing (0018, 1164) if the image is not calibrated or corrected. Otherwise, Pixel Spacing (0028,0030) shall have the corrected or calibrated values. The IHE Mammo profile may reintroduce double correction to other DX images which had been resolved by DICOM CP-586.

Further ambiguity issues are also introduced with the Estimated Radiographic Magnification Factor (0018,1114) for images acquired with a zoom bench versus images acquired without a zoom bench.

BRIEF SUMMARY OF THE INVENTION

Certain embodiments of the present invention provide methods and systems for calibrating a pixel spacing attribute value for X-ray mammography imaging based on a patient-specific breast thickness value.

Certain embodiments provide a method for patient specific pixel spacing calibration for mammography X-ray imaging. The method includes determining a patient specific breast thickness value for a particular patient being imaged by a mammography X-ray device having a radiation source and a detector and an associated imager pixel spacing value. The method also includes calibrating a pixel spacing attribute for a mammography X-ray image based on the patient specific breast thickness value, a radiation source to detector distance in the mammography X-ray device, and the image pixel spacing value.

Certain embodiments provide a system for calibration of X-ray mammography imaging parameters. The system includes an X-ray mammography unit for obtaining an X-ray mammography image. The X-ray mammography unit has a radiation source and a detector and an associated image pixel spacing value. The X-ray mammography unit providing a patient specific breast thickness value for a particular patient being imaged. The system also includes an image processing unit calibrating a pixel spacing attribute for the mammography X-ray image based on the patient specific breast thickness value, a radiation source to detector distance in the mammography X-ray device, and the image pixel spacing value.

Certain embodiments provide a computer readable medium having a set of instructions for execution on a computing device. The set of instructions includes a breast thickness routine determining a patient specific breast thickness value for a particular patient being imaged by a mammography X-ray device having a radiation source and a detector and an associated imager pixel spacing value. The set of instructions also includes a calibration routine calibrating a pixel spacing attribute for a mammography X-ray image based on the patient specific breast thickness value, a radiation source to detector distance in the mammography X-ray device, and the image pixel spacing value.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

Figure 1:
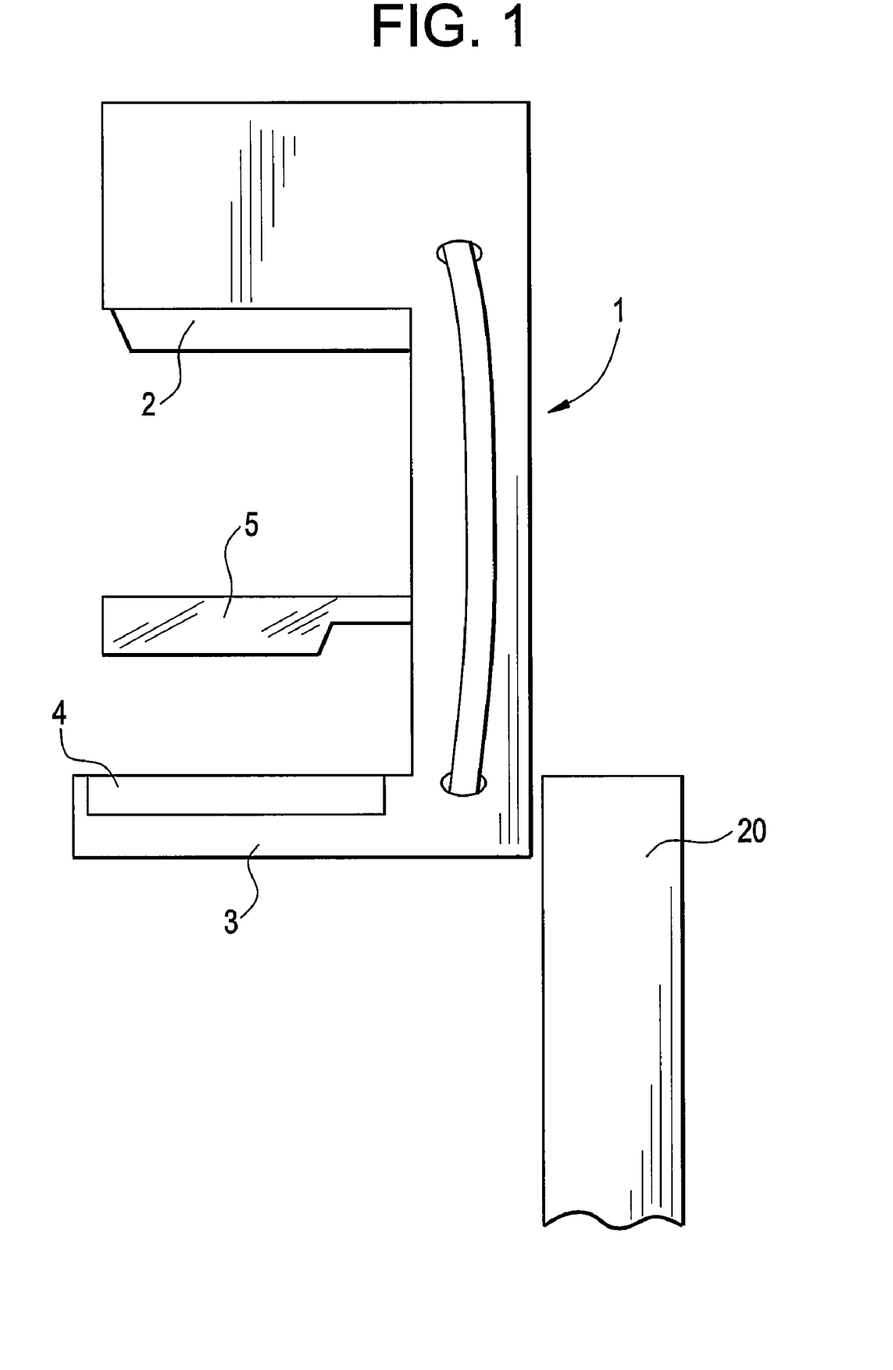
FIG. 1 illustrates an apparatus for mammography imaging.

As shown in FIG. 1, an apparatus for mammography imaging includes a C-shaped arm 1, which has a radiation source 2, such as an X-ray tube, at one of its ends, and which, at its other end, has an image acquisition device 4 for image acquisition, such as a cassette tray (e.g., a Potter Bucky tray, etc.) or digital detector. The end of the C-arm 1 having the image acquisition device 4 may also include a support device 3, such as a breast support plate to support a breast for mammography imaging, which can be removable if desired. A compression device 5, such as a plate or pad, is adjustable in height relative to support plate 3 and is provided facing plate 3. The C-shaped arm 1 is mounted on a frame 20 relative to which the arm 1 can be pivoted, particularly around a horizontal axis, for example.

Mammography images are generally taken with the patient standing upright facing towards the apparatus. The operator positions the breast on the plate 3, in such a way as to spread the breast as evenly as possible, and then compresses the breast using plate 5. In this way, one tries to enter the largest possible portion of the breast within the X-ray beam and thus to obtain the greatest possible coverage of the breast being examined. X-ray mammography images may be obtained of the positioned breast.

Additionally, breast position may be adjusted using the support 3 and compression device 5. A breast may be centered and/or positioned off-center between the radiation source 2 and the acquisition device 4, for example.

In certain embodiments, compression plates or paddles 5 may be removed and replaced depending upon a type of imaging, positioning, etc., desired. For example, square paddles, rectangular paddles, round paddles, paddles with holes, paddles of different sizes, etc., may be used in positioning the breast.

In certain embodiments, a zoom bench or stand can be used with the image acquisition device 4 for increased magnification of the breast in imaging. For example, a magnification plate may be latched or otherwise positioned onto or above a receptor or other acquisition device 4 to create more distance between the breast and the acquisition device 4.

Certain embodiments provide a calibration algorithm that takes into consideration an individual patient's breast size to achieve better accuracy in measurement. The presently technology is consistent with current DICOM standards and allows a user to compare distance measurements made on an image display with software tools with manual measurements made on printed films, for example.

Certain embodiments help address certain ambiguity issues in the current IHE Mammo profile draft document, in addition to double correction with mammography images acquired using a zoom stand.

In the IHE Mammo Integration Profile, Imager Pixel Spacing (0018,1164) and Estimated Radiographic Magnification Factor (0018,1114) are used to estimate a physical size of image pixels in a patient body.

In certain embodiments, an Imager Pixel Spacing (0018, 1164) value is to be filled according to a DICOM definition for this DICOM Type 1 attribute. The definition species that Imager Pixel Spacing is a physical distance measured at a front plane of a detector housing between a center of each image pixel specified by a numeric pair—row spacing value (delimiter) column spacing value in millimeters. The value of this attribute should not be adjusted to account for correction due to an effect of geometric magnification or calibration against an object of known size. Pixel Spacing (0028,0030) is specified for that purpose.

Pixel Spacing (0028,0030) is to be filled according to a DICOM definition for this DICOM Type 1C attribute. The definition specifies that Pixel Spacing is a physical distance in a patient between a center of each pixel, specified by a numeric pair—adjacent row spacing (delimiter) adjacent column spacing in millimeters.

A Pixel Spacing Calibration Type (0028,0402) is to be filled according to a DICOM definition for this DICOM Type 3 attribute. The definition specifies that Pixel Spacing Calibration Type is a type of correction for an effect of geometric magnification or calibration against an object of known size.

A Pixel Spacing Calibration Description (0029,0404) is to be filled according to a DICOM definition for this DICOM Type 1C attribute. The definition specifies that Pixel Spacing Calibration Description is a free text description of a type of correction or calibration performed. According to DICOM, a Pixel Spacing Calibration Description is required if Pixel Spacing Calibration Type (0028,0402) is present.

An Estimated Radiographic Magnification factor (0018, 1114) DICOM Type 3 is to be set to 1 for images acquired without an optical magnification stand, and to a zoom factor of the magnification stand itself for images acquired with the optical magnification stand.

Patient specific and machine specific calibration is to be reflected in the Pixel Spacing (0028,0030) and explained in the Pixel Spacing Calibration Type (0028,0402) and the Pixel Spacing Calibration Description (0029,0404).

According to DICOM, Image Display and Filming software first looks for Pixel Spacing (0028,0030) Type 1C first. If that does not exist, then the software looks for Imager Pixel Spacing (0018,1164) Type 1. This logic is consistent with DICOM CP-586 in that (0028, 0030) Pixel Spacing takes precedence over (0018, 1164) Image Pixel Spacing if both values exist in an image header.

As outlined, for example, in the DICOM Conformance Statement for GE Senographe systems, a DX Detector Distance Source to Patient (0018,1111) Type 3 Implementation limitation is provided. In magnification mode, this distance value is equal to a distance in millimeters from the radiation source to a theoretical average breast height (e.g., 20 mm above the breast support). In contact mode, the value is equal to the distance in millimeters from the source to the detector plane. An Estimated Radiographic Magnification factor (0018,1114) Type 3 and a Distance Source to Entrance (0040, 0306) are computed based on a Distance Source to Patient (0018,1111).

Additionally, a DX Detector Imager Pixel Spacing (0018, 1164) Type 1 Implementation limitation is provided. This value is equal to a physical distance measured at the theoretical average breast height (e.g., 20 mm above the breast support) between the centers of each projected image pixel.

Due to a large variation in patient breast sizes, compressed breast thickness can vary from less than 28 mm to more than 78 mm, for example. Instead of a "theoretical average breast height (e.g., 20 mm above the breast support)", certain embodiments use a middle point of a compressed breast as a calibration plane for Mammo X-Ray systems. Additionally, such "in patient" calibration can be stored in a DICOM Pixel Spacing (0028,0030) attribute with DICOM Enumerated Value GEOMETRY in a Pixel Spacing Calibration Type (0028,0402) attribute.

For example, a Mammo X-Ray system with an Imager Pixel Spacing of 0.1 mm according to DICOM definition at the front plane of the detector housing. A Distance Source to Detector is 660 mm. The Mammo system detects a patient's compressed breast thickness for a left craniocaudal (LCC) View to be 66 mm. A calibration plane should be at 33 mm above the breast support.

Without a zoom stand, the "in patient" Pixel Spacing is 0.1*(660−33)/660=0.95. Thus, parameters are as follows:
 (0018, 1114) Estimated Radiographic Magnification 1.0
 (0018, 1164) Imager Pixel Spacing 0.1
 (0028, 0030) Pixel Spacing 0.095

With zoom stand 300 mm high, the "in patient" Pixel Spacing is 0.1*(660−300−33)/660=0.0495. Thus, parameters are as follows:
 (0018, 1114) Estimated Radiographic Magnification 1.8
 (0018, 1164) Imager Pixel Spacing 0.1
 (0028, 0030) Pixel Spacing 0.0495

Thus, certain embodiments provide a calibration algorithm that takes into consideration an individual patient's breast size over a theoretical value to achieve better accuracy. The proposed use of the Pixel Spacing (0028,0030) parameter is consistent with the current DICOM standards and allows a user to compare distance measurements made on image display using software tools with manual measurements made on printed films, for example.

In certain embodiments, compressed breast thickness is measured and available on a digital Mammo X-ray system. Thus, certain embodiments can be implemented as a software enhancement upgrade without hardware cost. Legacy X-Ray systems can be upgraded with this backward compatible enhancement. Image review workstations, such as review workstations that follow DICOM CP-586, can take advantage of the new calibration while still being compatible with the images acquired from most legacy implementations (e.g., GE Senographe systems and Hologic Mammo X-Ray systems).

Rather than using the Estimated Radiographic Magnification factor (0018,1114) DICOM Type 3 optional value to correct the values in Imager Pixel Spacing (0018,1164), as proposed in the current IHE Mammo profile draft but which will result in double correction for many legacy images acquired with a magnification stand, calibration using individual breast size corrects Imager Pixel Spacing values without overcorrecting for magnification.

Certain embodiments take into account existing information about a patient rather than using theoretical, average or otherwise artificially created information regarding breast size to determine pixel spacing. The calibration calculation provides a "default" value based on breast size information. In certain embodiments, a user may accept or edit the generated value. The calibration calculation based on individual patient breast size provides a more acceptable and customizable calibration and helps avoid double correction of image information from a Mammo X-ray system. By accepting this value that changes appropriately with each patient and not having to input the value from manual measurement or visual estimation of breast size or reliance on a global "average," auto calibration algorithms may be more repeatable, more accurate, and more automatic, for example.

After calibration has been completed, medical personnel may use the imaging system and/or images produced in the system for a variety of applications. For example, further images may be obtained, obtained images may be used in non-invasive or invasive procedures such as cardiac catheterization, surgical navigation and/or surgical planning may be executed, and/or other medical procedure(s) may be performed. Image data may be processed based on the computed calibration factor, for example.

Figure 2:
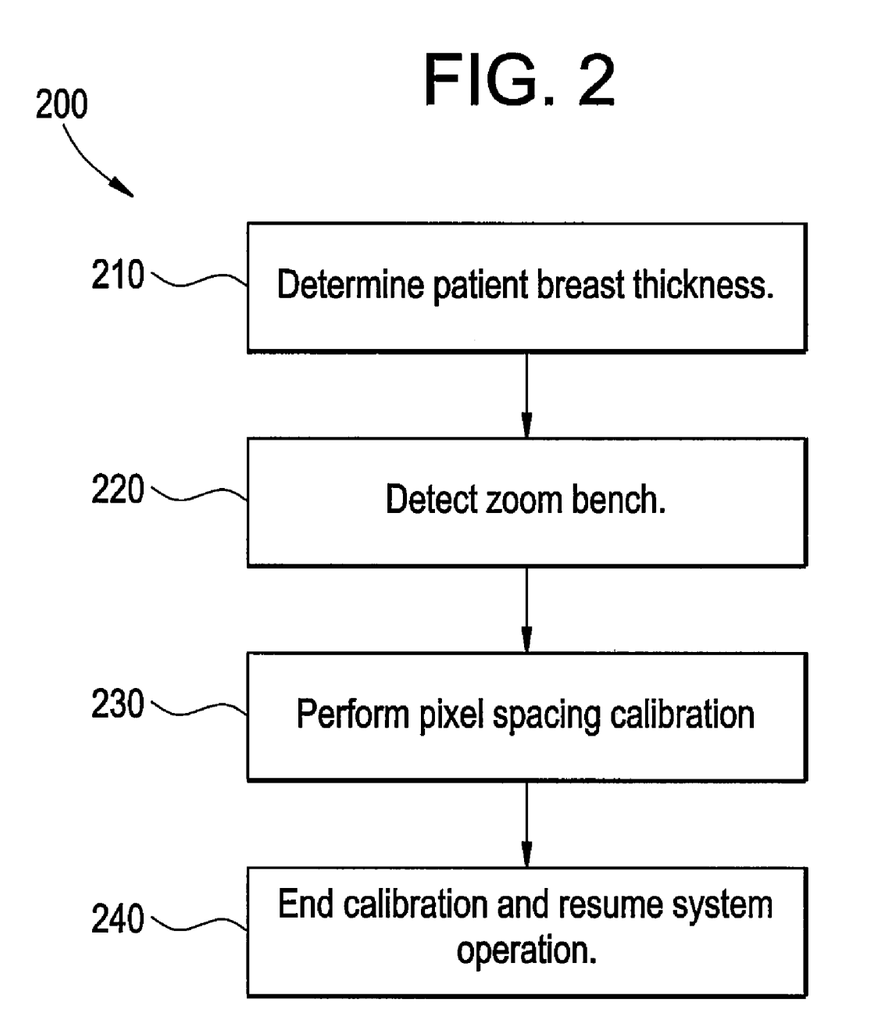
FIG. 2 illustrates a flow diagram for a method for patient-specific pixel spacing calibration for X-ray mammography systems in accordance with an embodiment of the present invention.

FIG. 2 illustrates a flow diagram for a method 200 for patient-specific pixel spacing calibration for X-ray mammography systems in accordance with an embodiment of the present invention. At step 210, a patient's breast thickness is determined. For example, the patient's breast thickness may have been previously measured or calculated. Alternatively, patient breast thickness may be measured at the time of image calibration.

At step 220, presence or absence of a zoom bench is detected. A zoom or magnification bench/stand provides increased zooming options in a resulting image and affects the calibration calculation. A zoom bench may be positioned with respect to an image acquisition device, such as a receptor, and below the breast, for example.

At step 230, calibration of pixel spacing is performed for the mammography imaging system. Appropriate calibration value(s) are calculated based on a function applied to the available data. As an example, a breast thickness value is presented to a user. The user may accept the value or modify the value. Alternatively, the imaging system may automatically use the value without user input. Calibration then proceeds using the breast thickness value. In certain embodiments, calibration of Pixel Spacing involves a plurality of parameters including Imager Pixel Spacing, source-to-detector distance, breast thickness, and zoom stand-to-detector distance. For example, $$PixelSpacing = ImagerPixelSpacing \times \frac{SourceToDetectorDistance - 1/2 BreastThickness}{SourceToDetectorDistance}$$

For example, if Imager Pixel Spacing=0.1 mm, Source-to-Detector Distance is 660 mm, compress breast thickness is 66 mm (so that a calibration plane is half the breast thickness or 33 mm above the breast support), Pixel Spacing=0.1*(660−33)/660=0.95.

If a zoom stand is used, Pixel Spacing is calculated as $$PixelSpacing = ImagerPixelSpacing \times$$
$$\frac{SourceToDetectorDistance - StandHeight - 1/2 BreastThickness}{SourceToDetectorDistance}$$

For example, if Imager Pixel Spacing=0.1 mm, Source-to-Detector Distance is 660 mm, compress breast thickness is 66 mm (so that a calibration plane is half the breast thickness or 33 mm above the breast support), and a zoom stand is 300 mm high, Pixel Spacing 0.1*(660−300−33)/660=0.0495.

At step 240, calibration ends and regular system operation may proceed. For example, mammography imaging of the breast may proceed following the calibration, or the calibration may occur after image(s) have been obtained but before image processing occurs. Following calibration, calibrated images may be used for a variety of purposes. Calibrated images may be processed and/or reviewed by a radiologist, for example.

One or more of the steps of the method 200 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 3:
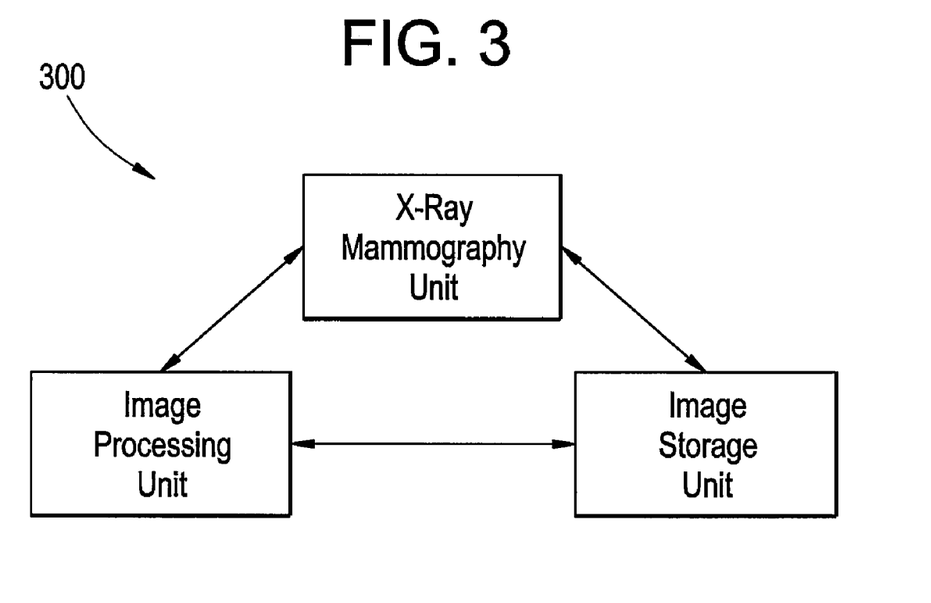
FIG. 3 illustrates an X-ray Mammo calibration system in accordance with an embodiment of the present invention.

Certain embodiments may be implemented using a processing device in communication with a Mammo X-ray system and/or associated processing/storage such as a Picture Archiving and Communication System (PACS) or a Radiology Information System (RIS). As an example, FIG. 3 illustrates an X-ray Mammo calibration system 300 including an X-ray mammography unit 310, an image processing unit 320, and an image storage unit 330. The components of the system 300 may be implemented in software, hardware, and/or firmware. The components of the system 300 may be implemented separately and/or integrated in various combinations. For example, the image processing unit 320 may be combined with the X-ray mammography unit 310. The image processing unit 320 may also be combined with the image storage unit 330, for example.

The mammography unit 310 obtains a mammography image of a patient breast. The image data is stored at the image storage unit 330. Before or after the image data is stored at the storage unit 330, the image data may be processed at the image processing unit 320. Image processing may include pixel spacing calibration for the patient image data from the mammography imaging unit 310. Alternatively, calibration may occur at the mammography unit 310 for a particular patient prior to acquisition of the image data for that patient. Pixel spacing calibration can occur using Imager Pixel Spacing, source-to-detector distance, breast thickness, and zoom stand-to-detector distance (if a zoom stand is present), as described above.

Thus, certain embodiments accommodate a variety of patient body types and breast sizes. Certain embodiments increase speed of auto calibration usage while using a more accurate estimation of the size of the patient breast being imaged.

Thus, certain embodiments provide a technical effect of more accurate breast size determination and pixel spacing calibration for mammography imaging. Certain embodiments may be used in conjunction with hardware and/or software for X-ray Mammo machines, such as GE Senographe 2000D, DS and Essential systems, Hologic Mammo systems, and Siemens. Mammo systems. Image Display and Filming workstations, such as GE SenoAdvantage, RA1000 and CDPS, can take advantage of the new calibration made by new Mammo X-Ray Machines while compatible with images acquired from most legacy implementations.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any machine-readable media for accomplishing its operations. As noted above, the embodiments of the present invention may be implemented using an existing computer processor, or by a special purpose computer processor incorporated for this or another purpose or by a hardwired system in conjunction with an X-ray mammography imaging system.

As noted above, embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represents examples of corresponding acts for implementing the functions described in such steps.

For example, in certain embodiments a computer readable medium having a set of instructions for execution on a computing device includes a breast thickness routine determining a patient specific breast thickness value for a particular patient being imaged by a mammography X-ray device having a radiation source and a detector and an associated imager pixel spacing value. The set of instructions also includes a calibration routine calibrating a pixel spacing attribute for a mammography X-ray image based on the patient specific breast thickness value, a radiation source to detector distance in the mammography X-ray device, and the image pixel spacing value.

For example, the pixel spacing attribute may be calculated using the following equation:

$$PixelSpacing = ImagerPixelSpacing \times \frac{SourceToDetectorDistance - 1/2 BreastThickness}{SourceToDetectorDistance}.$$

In certain embodiments, the calibration routine calibrates the pixel spacing attribute based on a presence of a zoom stand in the mammography X-ray device. For example, the pixel spacing attribute may be calculated using the following equation:

$$PixelSpacing = ImagerPixelSpacing \times \frac{SourceToDetectorDistance - StandHeight - 1/2 BreastThickness}{SourceToDetectorDistance}.$$

In certain embodiments, the calibration routine allows a user to at least one of approve and edit the patient specific breast thickness value. In certain embodiments, the calibration routine applies the calibrated pixel spacing attribute to the mammography X-ray image.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any calibration system for mammography imaging. Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A method for patient specific pixel spacing calibration for mammography X-ray imaging, said method comprising:
    determining a patient specific breast thickness value for a particular patient being imaged by a mammography X-ray device having a radiation source and a detector and an associated imager pixel spacing value; and
    calibrating a pixel spacing attribute for a mammography X-ray image based on the patient specific breast thickness value, a radiation source to detector distance in the mammography X-ray device, and the image pixel spacing value.

2. The method of claim 1, wherein the pixel spacing attribute is calculated using $$PixelSpacing = ImagerPixelSpacing \times \frac{SourceToDetectorDistance - 1/2BreastThickness}{SourceToDetectorDistance}.$$

3. The method of claim 1, further comprising detecting a presence of a zoom stand in the mammography X-ray device.

4. The method of claim 3, wherein the pixel spacing attribute is calculated using $$PixelSpacing = ImagerPixelSpacing \times$$
$$\frac{SourceToDetectorDistance - StandHeight - 1/2BreastThickness}{SourceToDetectorDistance}.$$

5. The method of claim 1, further comprising allowing a user to at least one of approve and edit the patient specific breast thickness value.

6. The method of claim 1, further comprising applying the calibrated pixel spacing attribute to the mammography X-ray image.

7. The method of claim 1, further comprising storing the mammography X-ray image after the calibrated pixel spacing attribute has been applied.

8. A system for calibration of X-ray mammography imaging parameters, said system comprising:
    an X-ray mammography unit for obtaining an X-ray mammography image, the X-ray mammography unit having a radiation source and a detector and an associated image pixel spacing value, the X-ray mammography unit providing a patient specific breast thickness value for a particular patient being imaged; and
    an image processing unit for calibrating a pixel spacing attribute for the mammography X-ray image based on the patient specific breast thickness value, a radiation source to detector distance in the mammography X-ray device, and the image pixel spacing value.

9. The system of claim 8, further comprising an image storage unit storing the mammography X-ray image after the calibrated pixel spacing attribute has been applied.

10. The system of claim 8, wherein the pixel spacing attribute is calculated using $$PixelSpacing =$$
$$ImagerPixelSpacing \times \frac{SourceToDetectorDistance - 1/2BreastThickness}{SourceToDetectorDistance}.$$

11. The system of claim 8, further comprising detecting a presence of a zoom stand in the mammography X-ray device.

12. The system of claim 11, wherein the pixel spacing attribute is calculated using $$PixelSpacing = ImagerPixelSpacing \times$$
$$\frac{SourceToDetectorDistance - StandHeight - 1/2BreastThickness}{SourceToDetectorDistance}.$$

13. The system of claim 8, wherein the image processing unit prompts a user to at least one of approve and edit the patient specific breast thickness value.

14. The system of claim 8, wherein the image processing unit applies the calibrated pixel spacing attribute to the mammography X-ray image.

15. A computer readable medium having a set of instructions for execution on a computing device, said set of instructions comprising:
    a breast thickness routine determining a patient specific breast thickness value for a particular patient being imaged by a mammography X-ray device having a radiation source and a detector and an associated imager pixel spacing value; and
    a calibration routine calibrating a pixel spacing attribute for a mammography X-ray image based on the patient specific breast thickness value, a radiation source to detector distance in the mammography X-ray device, and the image pixel spacing value.

16. The computer readable medium of claim 15, wherein the pixel spacing attribute is calculated using $$PixelSpacing =$$
$$ImagerPixelSpacing \times \frac{SourceToDetectorDistance - 1/2BreastThickness}{SourceToDetectorDistance}.$$

17. The computer readable medium of claim 15, wherein the calibration routine calibrates the pixel spacing attribute based on a presence of a zoom stand in the mammography X-ray device.

18. The computer readable medium of claim 17, wherein the pixel spacing attribute is calculated using $$PixelSpacing = ImagerPixelSpacing \times \frac{SourceToDetectorDistance - StandHeight - 1/2 BreastThickness}{SourceToDetectorDistance}.$$

19. The computer readable medium of claim 15, wherein the calibration routine allows a user to at least one of approve and edit the patient specific breast thickness value.

20. The computer readable medium of claim 15, wherein the calibration routine applies the calibrated pixel spacing attribute to the mammography X-ray image.

* * * * *